(12) United States Patent
Essiger

(10) Patent No.: US 6,302,885 B1
(45) Date of Patent: Oct. 16, 2001

(54) BONE NAIL

(76) Inventor: Holger K. Essiger, Speckweg 3, D-30900 Wedemark (DE)

( * ) Notice: Subject to any disclaimer, the term of this patent is extended or adjusted under 35 U.S.C. 154(b) by 0 days.

(21) Appl. No.: 09/232,148

(22) Filed: Jan. 15, 1999

(30) Foreign Application Priority Data

Jan. 15, 1998 (DE) .............................................. 198 01 219

(51) Int. Cl.⁷ .............................................. A61B 17/56
(52) U.S. Cl. .............................................. 606/72; 606/73
(58) Field of Search .................... 606/73–80, 60–72, 606/94–95, 104–105; 623/16–17; D8/385–395; 411/451, 452, 456, 455, 482, 487, 489, 493

(56) References Cited

U.S. PATENT DOCUMENTS

| | | | | |
|---|---|---|---|---|
| 74,501 | * | 2/1868 | Champlin | 606/451 |
| 895,080 | * | 8/1908 | Eisenreich | 411/465 |
| 1,100,252 | * | 6/1914 | O'Neill | 411/456 |
| 1,733,008 | * | 10/1929 | Foos | 411/452 |
| 1,978,145 | * | 10/1934 | Rosenberg | 411/452 |
| 2,696,817 | * | 12/1954 | Prevo | 606/72 |
| 3,618,447 | * | 11/1971 | Goins | 411/456 |
| 4,846,655 | * | 7/1989 | Gulley | 411/425 |
| 4,873,976 | * | 10/1989 | Schreiber | 128/334 |
| 5,492,452 | | 2/1996 | Kirsch et al. . | |
| 5,562,704 | * | 10/1996 | Tamminmaki et al. | 606/213 |

FOREIGN PATENT DOCUMENTS

| | | |
|---|---|---|
| 0 611 557 | 8/1994 | (EP) . |
| 0 714 643 | 6/1996 | (EP) . |
| 2 681 777 | 4/1996 | (FR) . |
| 2 731 610 | 9/1996 | (FR) . |

* cited by examiner

Primary Examiner—David O. Reip
Assistant Examiner—Lien Ngo
(74) Attorney, Agent, or Firm—R. W. Becker & Associates; R. W. Becker

(57) ABSTRACT

A bone nail has a shaft and a head connected to one end of the shaft. The shaft tapers in a direction away from the head. The shaft has at least one projection extending at least over a portion of the length of the shaft. The projections can be barbs or ridges along the length of the shaft.

20 Claims, 1 Drawing Sheet

BONE NAIL

This application claims a benefit to the German patent application Ser. No. 19801219.5 filed on Jan. 15, 1998.

BACKGROUND OF THE INVENTION

The present invention relates to a bone nail for bone surgery, especially for attachment of membranes, foils, and splints, wherein the bone nail comprises a shaft and a preferably plate-shaped head.

With known bone nails having a shaft with a circular cross-section, driving of the nails is difficult and is usually not made easier even when driving is to be facilitated by preboring the attachment location. Also, preboring the attachment location requires additional time and, furthermore, the shafts have the tendency to bend laterally and often are not capable of securing the nail properly when in its final position. These disadvantages are especially pronounced when these nails are used for securing foils, membranes and similar thin-walled elements used in surgery because such bone nails for such thin-walled elements have a comparably small shaft length which is usually within the millimeter range.

It is therefore an object of the present invention to eliminate these disadvantages or to at least reduce them considerably. Accordingly, the aforementioned nails are to be improved such that a better, faster, and simpler driving action can be achieved and/or, after securing, undesirable loosening or falling out of the nail is to be prevented.

SUMMARY OF THE INVENTION

As a solution to this object the nails are provided with a shaft that at least over a portion of its length is provided with one or more projections which are expediently angular, especially provided with sharp edges, and extending in the longitudinal direction of the shaft, but which also may be arranged in rows preferably arranged in the longitudinal direction of the shaft.

These projections surprisingly allow for a relatively simple driving of the nails which can be explained by a cutting effect of the projections. When these projections are arranged individually, they can produce in addition small anchoring locations within the bone in order to prevent loosening of the nail connection. It is advantageous in this context when the projections do not impede or impede only minimally the driving action of the nail, but in the driven state of the nail provide a barb-like effect, for which purpose they are embodied in the form of saw teeth.

On the other hand, it is possible to embody the projections such that they extend as ridges over a portion of the length of the shaft. Accordingly, when selecting the cross-section of the shafts, this can be taken into consideration by providing the shafts within the desired portions with a triangular, square, rectangular, star-shaped or similar design.

An especially advantageous suggestion is to provide the shafts over a portion of their length with ridge-shaped angular projections and over another portion of their length with individual barb-like projections, optionally arranged in rows, whereby preferably the ridges are provided at the free end of the shaft and the barbs are provided in a portion of the shaft adjacent to the head of the bone nail. This design of the shaft provides the aforementioned advantages with respect to driving the nail while in the portion adjacent to the head the means (barbs) are provided to prevent loosening or falling out of the nail.

BRIEF DESCRIPTION OF THE DRAWINGS

The object and advantages of the present invention will appear more clearly from the following specification in conjunction with the accompanying drawings, in which:

FIG. 7 shows a section along the line VII—VII of FIG. 1;

DESCRIPTION OF PREFERRED EMBODIMENTS

Figure 1:
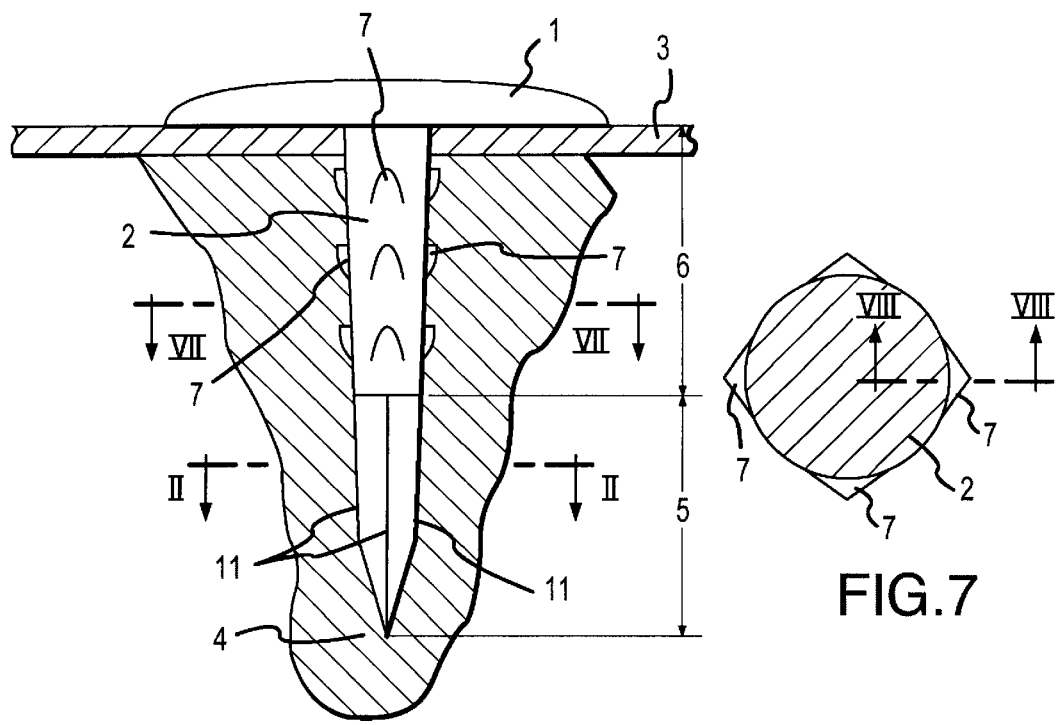
FIG. 1 shows in cross-sectional view a bone nail in its effective position for fastening a foil or membrane to bone.

The present invention will now be described in detail with the aid of several specific embodiments utilizing FIGS. 1 through 8.

The bone nail which is comprised of steel etc., especially titanium, has a plate-shaped head 1 and a slim shaft 2 which penetrates the membrane 3 to be attached and engages the bone 4. The shaft 2 has two portions 5, 6 of substantially the same length whereby the portion 5 is designed such that it facilitates driving of the nail, preferably without preboring, into the bone. The portion 6 is designed such that it can prevent loosening or even falling out of the nail.

Figure 8:
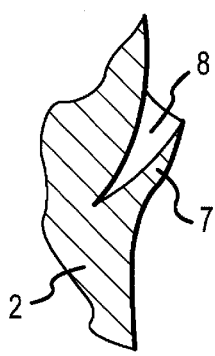
FIG. 8 shows a partial longitudinal section (along section line VIII—VIII of FIG. 7 of the nail shaft according to FIG. 1 in the area of barb-like projections at the nail shaft.

The portion 6 is provided with a number of individual projections 7 distributed about the circumference of the shaft 2 and preferably arranged in vertical rows (a random or scattered arrangement is also possible) whereby the projections 7 are barb-like and have pointed ends facing the head 1. These projections or barbs 7 are designed according to the so called file cut for coarse files (wood working files) and are produced by bending material of the shaft 2 outwardly. The projections 7, as can be seen in FIG. 8, are in section and in a side view tapered toward their free end but also taper in the direction toward their free end when viewed in a view according to FIG. 1.

This provides for an especially excellent fixation of the nail within the bone. The recesses or depressions which are formed by bending the projections 7 out of the shaft are indicated by reference number 8.

Figure 4:
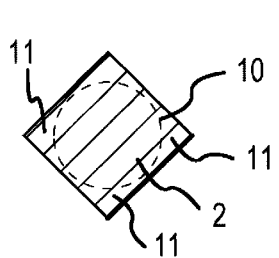
FIGS. 4, 5, and 6 show different shaft cross-sections.
Figure 2:
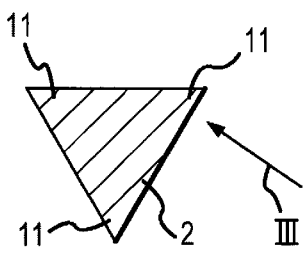
FIG. 2 shows a section along the line II—II of FIG. 1.

The portion 5 which is designed to facilitate driving of the shaft 2 into the bone, has also projections relative to a known round shaft cross-section (compare dashed line 10 of FIG. 4). These projections are embodied as angular (pointed) ridges 11 extending in the longitudinal direction of the shaft 2 and have a substantially triangular cross-section. They can be embodied in a simple manner such that a triangular shaft cross-section according to FIG. 2 is provided but also by a square cross-section as shown in FIG. 4.

It was found that, surprisingly, the angular, respectively, pointed projections or ridges 11, when driving the bone nail into the bone 4, provide a certain cutting effect and thus cause a certain displacement action within the bone 4.

Figure 5:
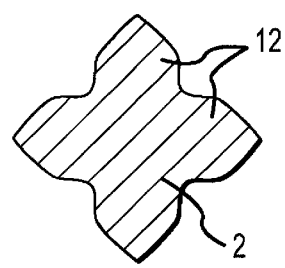

In certain applications, a substantially cross-shaped cross-sectional design of the shaft 2, as shown in FIG. 5, can be selected whereby the bars forming the cross of the cross-section also have pointed ends. Furthermore, it is possible to provide only two diametrically opposed projections 11 according to FIG. 6.

When there is no danger of undesirable loosening of the bone nails within the bone, the barb-like projections can be omitted. The projections 11 can then be provided as continuous ridges along the length of the shaft 2.

When additional securing means are desired, in addition to the longitudinal ridges along the length of the shaft individual barb-like projections 7 can be selected (as shown in FIG. 1). It is then expedient to provide at the lower end of the shaft (portion 5) means for facilitating driving of the nail into the bone.

Figure 3:
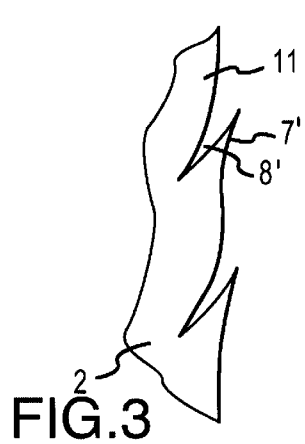
FIG. 3 shows a partial view of the bone nail in the direction of arrow III of FIG. 2.
Figure 6:
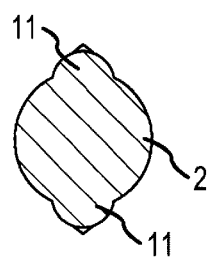

As can be seen in FIG. 3, the ridge-shaped projections 11 can also be provided with barbs or similar means. The projections are indicated with reference numeral 7' and the depressions therebehind are indicated with reference numeral 8'.

It should be noted that the inventive bone nail can also be used for attachment of splints whereby the bone nail usually penetrates a cutout (bore) of the splint in order to provide for the securing action.

The specification incorporates by reference the disclosure of German priority document 198 01 219.5 of Jan. 15, 1998.

The present invention is, of course, in no way restricted to the specific disclosure of the specification and drawings, but also encompasses any modifications within the scope of the appended claims.

What is claimed is:

1. A bone nail comprising:

a shaft (2);

a head (1) connected to one end of said shaft (2);

said shaft (2) having a plurality of projections (7, 11) extending at least over a portion of the length (5, 6) of said shaft (2):

first ones of said projections (11) positioned at a first portion (5) of said shaft (2) and second ones of said projections (7) positioned at a second portion (6) of said shaft (2), wherein said first projections (11) are elongate ridges extending in a longitudinal direction of said shaft (2) and wherein said second projections (7) are barbs; wherein said barbs (7, 7') are formed by bending material of said shaft outwardly.

2. A bone nail according to claim 1, wherein said projections (11) at said first portion are angular or pointed in a radially outward direction of said shaft (2).

3. A bone nail according to claim 2, wherein said projections (11) at said first portion form an acute angle in said radially outward direction.

4. A bone nail according to claim 1, comprising a plurality of said projections (7) arranged individually at the circumference of said shaft (2).

5. A bone nail according to claim 5, wherein said projections (7) are aligned in a longitudinal direction of said shaft (2).

6. A bone nail according to claim 1, wherein said barbs provide in a driving direction of said bone nail a smaller movement resistance than in a removal direction opposite to said driving direction.

7. A bone nail according to claim 6, wherein said barbs (7, 7') are formed by bending material of said shaft (2) outwardly.

8. A bone nail according to claim 1, wherein said first portion (6) of said shaft (2) having said ridges (11) is remote from said head (1).

9. A bone nail according to claim 1, wherein said barbs are formed by bending material of said shaft (2) outwardly, thereby forming respective recesses (8) between said barbs (7) and said shaft (2).

10. A bone nail according to claim 1, wherein said barbs (7), when viewed in a longitudinal section of said shaft (2) as well as in an end view of said shaft (2), taper in a direction toward a free end of said barbs.

11. A bone nail according to claim 1, wherein at least a portion of said shaft (2) has a triangular or quadrangular cross-section.

12. A bone nail according to claim 11, wherein said cross-section is square.

13. A bone nail according to claim 1, wherein at least a portion of said shaft (2) has a cross-shaped cross-section.

14. A bone nail according to claim 1, wherein two of said projections (11) are positioned diametrically opposite one another.

15. A bone nail according to claim 1, wherein said shaft (2) tapers in a direction away from said head (1).

16. A bone nail comprising:

a shaft (2), at least a portion of which as a round cross-section;

a head (1) connected to one end of said shaft (2);

said shaft (2) having a plurality of projections (7, 7'; 11) extending at least over a portion of the length (5, 6) of said shaft (2);

wherein first ones of said projections (11) are ridges extending in a longitudinal direction of said shaft (2) and second ones of said projections are barbs (7') provided on radially outer edges of said ridges (11).

17. A bone nail according to claim 16, wherein said barbs (7, 7'), when viewed in a longitudinal section of said shaft (2) as well as in an end view of said shaft (2), taper in a direction toward a free end of said barbs.

18. A bone nail according to claim 16, wherein said barbs provide in a driving direction of said bone nail a smaller movement resistance than in a removal direction opposite to said driving direction.

19. A bone nail according to claim 16, wherein said barbs (7, 7') are formed by bending material of said shaft (2) outwardly, thereby forming respective recesses (8') between said barbs (7') and said shaft (2).

20. A bone nail according to claim 16, wherein said shaft (2) tapers in a direction away from said head (1).

* * * * *